US009695456B2

(12) United States Patent
Teramura et al.

(10) Patent No.: US 9,695,456 B2
(45) Date of Patent: Jul. 4, 2017

(54) MICROORGANISM TESTING APPARATUS, METHOD AND PROGRAM

(71) Applicant: JNC CORPORATION, Tokyo (JP)

(72) Inventors: Hajime Teramura, Kanagawa (JP); Hiromi Osawa, Tokyo (JP); Ryuzo Kimura, Tokyo (JP); Ikuo Sato, Kanagawa (JP)

(73) Assignee: JNC CORPORATION, Tokyo (JP)

( * ) Notice: Subject to any disclaimer, the term of this patent is extended or adjusted under 35 U.S.C. 154(b) by 76 days.

(21) Appl. No.: 14/938,853

(22) Filed: Nov. 12, 2015

(65) Prior Publication Data

US 2016/0139027 A1      May 19, 2016

(30) Foreign Application Priority Data

Nov. 14, 2014    (JP) .................................. 2014-231905

(51) Int. Cl.
*G01N 35/00*   (2006.01)
*C12Q 1/02*    (2006.01)
(Continued)

(52) U.S. Cl.
CPC ................. *C12Q 1/02* (2013.01); *C12Q 1/04* (2013.01); *C12Q 1/06* (2013.01); *G01N 2035/0091* (2013.01)

(58) Field of Classification Search
CPC ........... G06K 9/00127; G06K 9/00134; G06K 9/0014; G01N 1/28; G01N 35/00029; G01N 2035/00108; G01N 35/00722; G01N 35/00732; G01N 35/00821; G01N 35/00831; G01N 35/00851;
(Continued)

(56) References Cited

U.S. PATENT DOCUMENTS

2002/0192742 A1    12/2002  Ushiyama et al.
2007/0141711 A1*    6/2007  Stephens et al. ............... 436/43
(Continued)

FOREIGN PATENT DOCUMENTS

JP    2000-270840 A    10/2000
JP    2012-080802 A     4/2012
WO       01/44437 A1    6/2001

OTHER PUBLICATIONS

Interscience, "Catalog: Scientific equipment for microbiology", retrieved Jun. 12, 2014, from URL: http://www.interscience.fr/IMG/pdf/interscience_scan_range_brochure_en_web.pdf, pp. 1-16.

*Primary Examiner* — Andrew W Johns
(74) *Attorney, Agent, or Firm* — Jianq Chyun IP Office (57) ABSTRACT

A solution is the microorganism testing apparatus equipped with a pre-processing unit in which, if a content of microorganism testing on a specific specimen is selected or input, testing conditions of the specimen read from a storage device in which testing information specifying the testing conditions of the specimen is stored are printed on a sheet-form medium to be used for testing of the specimen, and a post-processing unit in which, if an image of the medium is read, the testing conditions printed on the medium and a type of the medium preliminarily labelled on the medium are acquired from the image to output judgment results as to whether or not the testing conditions acquired from the image, and the type of the medium are compatible.

21 Claims, 10 Drawing Sheets

(51) Int. Cl.
*C12Q 1/04* (2006.01)
*C12Q 1/06* (2006.01)

(58) Field of Classification Search
CPC .. G01N 35/00861; G02B 21/34; G02B 21/36; G02B 21/365; C12M 1/34; C12M 1/3446; C12M 1/36; C12Q 1/02; C12Q 1/04; C12Q 1/045; C12Q 1/06; C12Q 1/08
See application file for complete search history.

(56) References Cited

U.S. PATENT DOCUMENTS

| | | | |
|---|---|---|---|
| 2015/0211987 A1* | 7/2015 | Burg et al. | G01N 21/27 356/402 |
| 2016/0124206 A1* | 5/2016 | Böse et al. | G02B 21/362 348/79 |

* cited by examiner

MEASURED DATA LIST

COLONY COUNTER APPLICATION

MENU | LIST | Measured data registration | Setup administration

Keyword:
Template selection:
Measurement dilution factor selection:
Status:

Data manual input: ○ OK  ○ NG
Testing input date: [   ] ~ [   ]
Result selection: ○ OK  ○ NG Checked data | Output | Delete

| Date and time of testing / Date and time of measurement | Template | Title | Product name | Ingredient name | Dilution factor | Number of colonies | Measurement results | Status |
|---|---|---|---|---|---|---|---|---|
| 2014/9/5 14:00 / 2014/9/6 14:00 | For aerobic plate count | September 4, 2014 General viable bacteria culture | Twice cooked pork lunch | Lettuce | Once | 200 (cfu/g(mL)) | NG | After measurement |
| 2014/9/5 14:00 | For coliform | September 4, 2014 E. coli culture | Twice cooked pork lunch | Lettuce | Once | 0 (cfu/g(mL)) | OK | After measurement |
| 2014/9/4 14:00 | For aerobic plate count | September 4, 2014 General viable bacteria culture | Twice cooked pork lunch | Lettuce | 100 times | – (cfu/g(mL)) | – | Before measurement |
| 2014/9/2 14:00 | For coliform | September 4, 2014 E. coli culture | Twice cooked pork lunch | White rice | Once | – (cfu/g(mL)) | – | Before measurement |
| 2014/9/3 14:00 | For aerobic plate count | September 4, 2014 General viable bacteria culture | Twice cooked pork lunch | Bell pepper | Once | 200 (cfu/g(mL)) | NG | After measurement |

MICROORGANISM TESTING APPARATUS, METHOD AND PROGRAM

CROSS-REFERENCE TO RELATED APPLICATIONS

This application is based upon and claims the benefit of priority of the prior Japanese Patent Application No. JP2014-231905, filed on Nov. 14, 2014, the entire contents of which are incorporated herein by reference.

TECHNICAL FIELD

The present disclosure relates to a microorganism testing apparatus, method and program.

DESCRIPTION OF THE BACKGROUND ART

In recent years, on a site of work for counting the number of microorganisms or the like, media with easy handling and showing various kinds of forms, or various automated equipment have been widely applied. For example, Patent literature No. 1 discloses a sheet-form medium with easy handling. Moreover, Patent literature No. 2 discloses an apparatus for automatically fishing a bacterial colony. Moreover, Patent literature No. 3 and Non-patent literature No. 1 disclose a colony counter being an apparatus for automating counting of the number of microorganisms in food or the like, and for picking up culture media on which colonies grow by means of an image pickup apparatus to automatically count the number of microorganisms grown on the media by image analysis.

DOCUMENT OF PRIOR ART

Patent Document

[Patent document 1] International Publication Pamphlet No. WO 01/044437 A.
[Patent document 2] Japanese Patent Application Laid-Open Publication No. 2012-080802.
[Patent document 3] Japanese Patent Application Laid-Open Publication No. 2000-270840.

Non Patent Document

[Non Patent document 1] Non-patent document No. 1: "Catalog: Scientific equipment for microbiology," interscience, [online], [retrieved, Jun. 12, 2014], Internet www.interscience.fr/IMG/pdf/interscience_scan_range_brochure_en_web.pdf).

SUMMARY

Technical Problems

Bacteriological testing in food or the like is conducted according to procedures as described below, for example. More specifically, first, a medium is prepared, and then testing information such as a species name of a specimen to be provided for testing and a dilution factor is described on the prepared medium. Then, a material prepared by treating and diluting the specimen is inoculated into the medium, and cultured, and then the number of microorganisms grown on the medium is counted. Then, the counted number of microorganisms is recorded together with specimen information. The bacteriological testing is conducted according to such procedures, and therefore when many foods are tested, a large amount of labor and time is needed in an actual state. Thus, a desire is expressed for not only automation of counting of the number of microorganisms but also rationalization of a series of complicated work related to testing.

Consequently, the disclosure provides a microorganism testing apparatus, a microorganism testing method and a non-transitory computer-readable recording medium stored with a microorganism testing program according to which work related to testing of microorganisms can be rationalized.

Solution to the Problems

In order to solve the problem described above, the present disclosure has been provided in which, if a content of microorganism testing on a specific specimen is selected or input, testing conditions of a relevant specific specimen are read from a storage device to print the conditions on a sheet-form medium, and if an image of the medium is read, the testing conditions and a type of the medium are acquired from the image to judge compatibility.

In detail, the disclosure is a microorganism testing apparatus equipped with a pre-processing unit in which, if the content of microorganism testing on the specific specimen is selected or input, the testing conditions of the specific specimen read from the storage device in which testing information specifying the testing conditions of the specimen is stored are printed on the sheet-form medium to be used for testing of the specific specimen, and a post-processing unit in which, if the image of the medium is read, the testing conditions printed on the medium and the type of the medium preliminarily labelled on the medium, are acquired from the image to output judgment results as to whether or not the testing conditions acquired from the image, and the type of the medium are compatible.

In a preparatory stage being pre-processing of the microorganism testing, the microorganism testing apparatus prints the testing conditions on the sheet-form medium to be used for testing of the specimen. The testing conditions to be printed on the medium are information read from the storage device in which the testing information specifying the testing conditions of the specimen is stored. Therefore, for example, when similar testing is repeated on a regular basis, the information can be reused, and preparatory work of the microorganism testing is saved. Then, if a person in charge of testing reads the testing conditions printed on the medium, the person can easily understand whether the medium is to be used for testing of any specimen. Therefore, for example, an error of wrong use of a different object is suppressed upon handling the specimen and the medium.

Further, in a data processing stage being post-processing of the microorganism testing, the microorganism testing apparatus analyzes the read image of the medium, and collates the testing conditions printed on the medium with labelling of the medium to output the results. Therefore, even if the wrong use of the medium occurs as described above, the apparatus can detect the wrong use to inform the person in charge thereof of the fact.

If the microorganism testing apparatus is applied, the work in the preparatory stage of the microorganism testing is saved as described above, and also the information to be printed on the medium by realization of work saving is effectively used for verification of testing in the data processing stage being the post-processing of the microorganism testing. Thus, the pre-processing and the post-processing are organically associated with each other to achieve overall rationalization of the work related to the testing of the microorganisms.

In addition, the pre-processing unit may print a symbol or a name representing the specific specimen, a dilution factor and a code produced by coding any other testing condition. If such a microorganism testing apparatus is applied, while information to be used for the post-processing in the microorganism testing is coded, the information to be understood upon handling the specimen of the medium is converted into a display form that can be recognized by the person in charge. Therefore, while the overall rationalization of the work related to the microorganism testing is achieved, the wrong use of the medium can be effectively prevented.

Moreover, an expiration date of the medium is preliminarily displayed on the medium, and the post-processing unit may further acquire, if the image of the medium is read, the expiration date displayed on the medium from the image to further output judgment results as to whether or not the expiration date acquired from the image has passed. If such a microorganism testing apparatus is applied, not only the wrong use of the medium but also erroneous processing of invalid tested result data can be suppressed.

Moreover, the post-processing unit may specify, if the image is read, the number of colonies grown on the medium, from the image. If such a microorganism testing apparatus is applied, an amount of work in the data processing stage being the post-processing of the microorganism testing can be reduced by using the image to be used for verification of the testing, and the overall rationalization of the work related to the microorganism testing can be achieved.

Moreover, in the testing conditions, a threshold value of quality determination of the number of colonies is further predetermined, and the post-processing unit may output the tested results of the specific specimen based on the specified number of colonies and the threshold value in the testing conditions. If such a microorganism testing apparatus is applied, judgment results of the tested results can be automatically obtained. Therefore, the overall rationalization of the work related to the microorganism testing can be achieved.

Moreover, the pre-processing unit may read, if the content of microorganism testing on the specific specimen is selected or input, the image of the medium to be printed, or may discriminate a shape or a size of the medium to be printed to further judge whether or not the testing conditions of the specific specimen read from the storage device, and the type of the medium to be printed are compatible. If such a microorganism testing apparatus is applied, culture of the microorganisms using an off-type medium can be prevented.

Moreover, the pre-processing unit may select, if the content of microorganism testing on the specific specimen is selected or input, from a plurality of kinds of media preliminarily arranged for the apparatus for applying printing onto the medium, the medium compatible with the testing conditions of the specific specimen read from the storage device to print the testing conditions on a selected medium. If such a microorganism testing apparatus is applied, work for exchanging the media is unnecessary in preparatory work for the microorganism testing, and when the plurality of kinds of media are handled in one-time preparatory work, the preparatory work is easy.

In addition, the disclosure can also be comprehended from an aspect of a method. For example, the disclosure may be a microorganism testing method which executes a pre-processing step, in which, if a content of microorganism testing on a specific specimen is selected or input, testing conditions of the specific specimen read from a storage device in which testing information specifying the testing conditions of the specimen is stored are printed on a sheet-form medium to be used for testing of the specific specimen, and executes a post-processing step, in which, if an image of the medium is read, the testing conditions printed on the medium and a type of the medium preliminarily labelled on the medium are acquired from the image to output judgment results as to whether or not the testing conditions acquired from the image, and the type of the medium are compatible.

Moreover, the disclosure can also be comprehended from an aspect of a non-transitory computer-readable recording medium stored with a computer program. For example, the disclosure may be a non-transitory computer-readable recording medium stored with a microorganism testing program that allows a computer to execute a pre-processing step, in which, if a content of microorganism testing on a specific specimen is selected or input, testing conditions of the specific specimen read from a storage device in which testing information specifying the testing conditions of the specimen is stored are printed on a sheet-form medium to be used for testing of the specific specimen, and to execute a post-processing step, in which, if an image of the medium is read, the testing conditions printed on the medium and a type of the medium preliminarily labelled on the medium are acquired from the image to output judgment results as to whether or not the testing conditions acquired from the image, and the type of the medium are compatible.

Effects of the Disclosure

According to a microorganism testing apparatus, a microorganism testing method and a non-transitory computer-readable recording medium having stored with a microorganism testing program as described above, work related to microorganism testing can be rationalized.

DESCRIPTION OF THE EXEMPLARY EMBODIMENTS

An embodiment according to the disclosure will be described below. The embodiment shown below is provided for illustrative purposes only, and a technical scope of the disclosure is not limited thereto.

Figure 1:
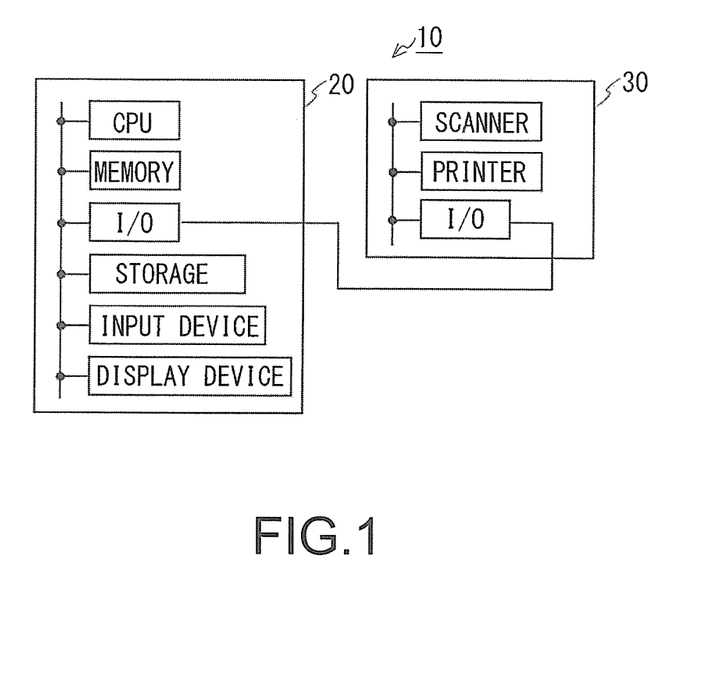
FIG. 1 is a diagram showing one example of a configuration diagram of a microorganism testing apparatus as related to the present embodiment.

FIG. 1 is a diagram showing one example of a configuration diagram of a microorganism testing apparatus as related to the present embodiment. As shown in FIG. 1, microorganism testing apparatus 10 is equipped with computer 20 and combination machine 30 combining a printer function and a scanner function. Computer 20 is equipped with CPU for performing various kinds of operation processing, storage devices such as a memory or a hard disk (storage), an input output terminal (I/O), an input device such as a keyboard, a mouse, a touchpad and a touch panel, and a display device such as a liquid crystal panel, and is information processing equipment in which computer 20 executes a computer program stored in the storage devices to realize various kinds of functions. Combination machine 30 is a device capable of printing data acquired from computer 20 on sheets, or reading information on a surface of a sheet-form material to produce image information.

In addition, as computer 20, a desktop type, a laptop type, a tablet type and various kinds of other types can be applied. Moreover, in microorganism testing apparatus 10 related to the present embodiment, combination machine 30 having both the printer function and the scanner function is illustrated, but microorganism testing apparatus 10 related to the present embodiment may use a printer and a scanner as a different form, in place of combination machine 30. Moreover, the scanner function may be of a flat head type, a sheet feed type for incorporating a sheet-form material, or a type in which an image pickup device arranged apart from a subject picks up a whole image of the subject (for example, a stand type and a type utilizing a camera built in a smartphone).

Figure 2:
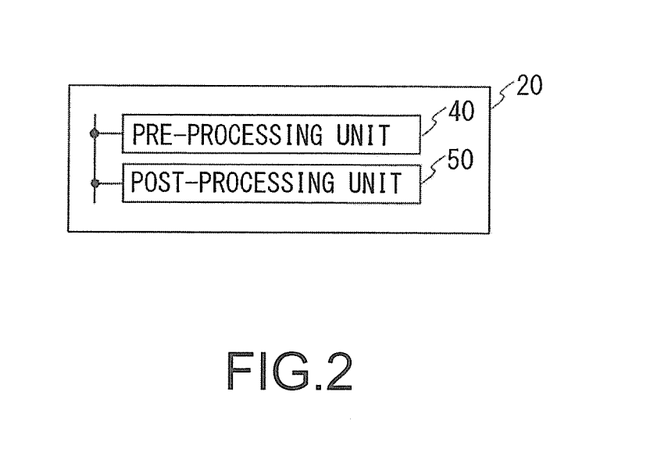
FIG. 2 is a diagram showing one example of a function block to be realized by a computer.

If computer 20 in microorganism testing apparatus 10 executes the computer program stored in the storage device, the application for realizing a function block as described below starts. FIG. 2 is a diagram showing one example of the function block to be realized by computer 20. If computer 20 executes the computer program stored in the storage device, computer 20 realizes various kinds of function units such as pre-processing unit 40 and post-processing unit 50.

Pre-processing unit 40 mainly takes charge of processing in which, if a content of microorganism testing on a specific specimen is selected or input, testing conditions of the specific specimen read from the storage device in which testing information specifying the testing conditions of the specimen is stored are printed on a sheet-form medium to be used for testing of the specific specimen. Moreover, post-processing unit 50 takes charge of processing in which, if an image of the medium is read, the testing conditions printed on the medium and a type of the medium preliminarily labelled on the medium are acquired from the image to output judgment results as to whether or not the testing conditions acquired from the image, and the type of the medium are compatible.

Figure 3:
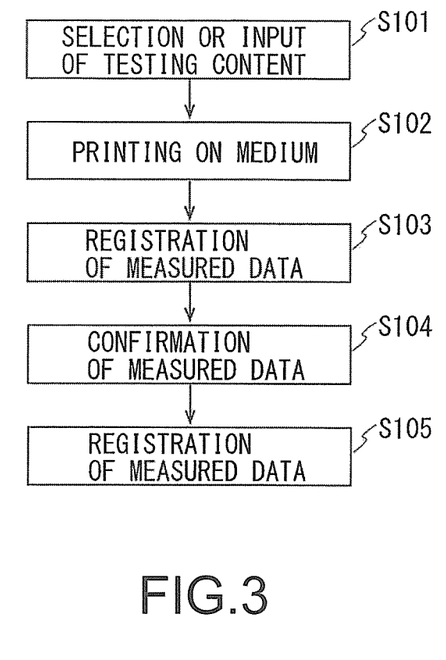
FIG. 3 is a diagram showing one example of a flowchart of a processing content to be realized by a computer.

Hereafter, the processing content to be realized by computer 20 is described. FIG. 3 is a diagram showing one example of a flowchart of the processing content to be realized by computer 20. The processing content to be realized by computer 20 is described along the flowchart in FIG. 3.

Figure 4A:
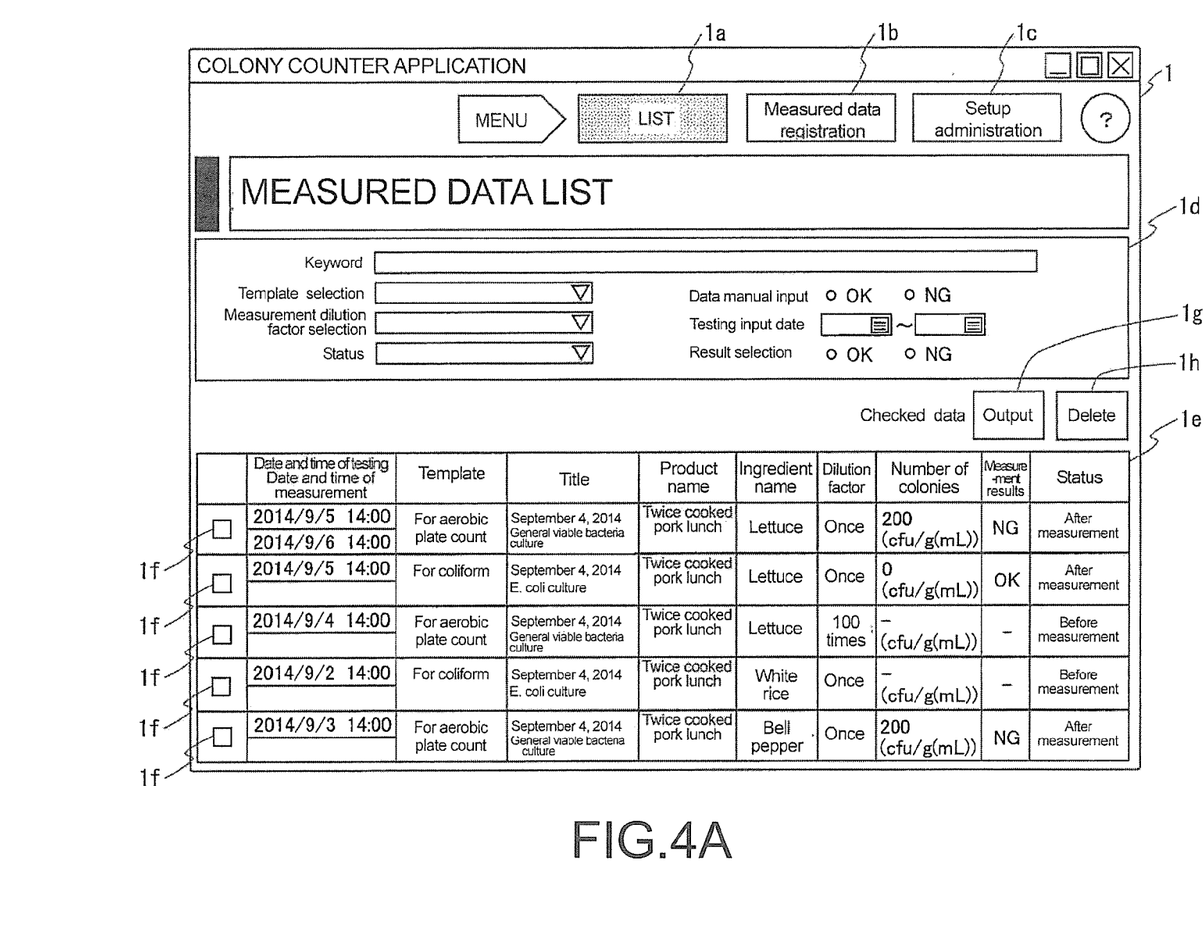
FIG. 4A is a diagram showing one example of a screen to be displayed on a display device if an application is started.

If the application is started, computer 20 displays, on the display device, a screen arranging menu buttons for selecting various kinds of operation and existing data. FIG. 4A is a diagram showing one example of the screen to be displayed on the display device if the application is started. If the application is started, computer 20 displays, on the display device, measured data list screen 1 appropriately arranging, for example, as shown in FIG. 4A, list button 1a for calling a list screen of measured data, measured data registration button 1b for calling a registration screen of the measured data, setup administration button 1c for calling an administration screen for performing various kinds of setup, measured data retrieval field 1d for retrieving the measured data, data list 1e in which existing registration data are arranged, output button 1g and deletion button 1h for outputting and deleting the data checked in check box 1f among respective measured data arranged on data list 1e.

The respective measured data arranged on data list 1e are preliminarily prepared by an administrator by using the administration screen to be called upon pushing setup administration button 1c, in which the data are preliminarily arranged in the form of a model in order to use the data of each item related to the testing content, such as a product name and an ingredient name of a testing object, a dilution factor, a template name showing a kind of a medium to be used, a date and time of testing and a title, for measurement work to be performed on a regular basis. For example, among the respective measured data arranged on data list 1e, third data from a top in which a status is "before measurement" show to the effect that lettuce used in a twice cooked pork lunch is to be tested, at 14:00, Sep. 4, 2014 in dilution by 100 times by using a medium for aerobic plate count.

Figure 4B:
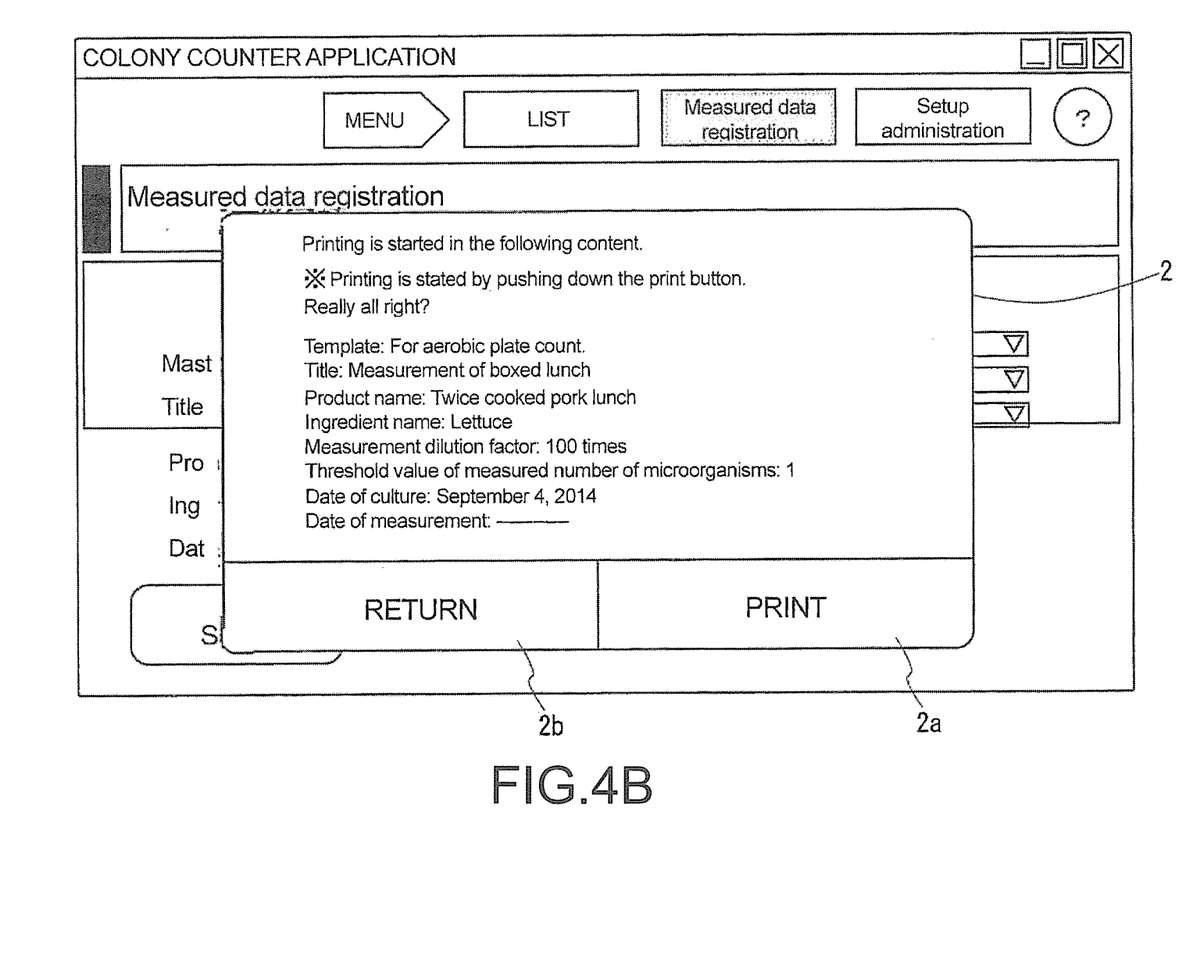
FIG. 4B is a diagram showing one example of a confirmation screen to be displayed on a display device upon applying printing onto a medium.

Here, if a person in charge of testing operates computer 20, and for example, among the respective measured data arranged in data list 1e, selects data of a desired test content, checks check box 1f and clicks output button 1g (S101), computer 20 executes processing as described below. FIG. 4B is a diagram showing one example of a confirmation screen to be displayed on the display device upon applying printing onto the medium. If the person in charge of testing operates computer 20, and for example, among the respective measured data arranged in data list 1e, checks check box 1f of the third data from the top, in which the status is "before measurement," and then clicks output button 1g, computer 20 displays, on the display device, confirmation screen 2 arranging, as shown in FIG. 4B, to the effect that the medium to be printed is for aerobic plate count, the test object is lettuce for the twice cooked pork lunch, the dilution factor is 100 times, the threshold value of the number of microorganisms is 1, and the date of testing is September 4, and print button 2a and return button 2b. Then, if the person in charge of testing operates computer 20 and clicks print button 2a, combination machine 30 incorporates the sheet-form medium set in a sheet tray to start printing, and prints the measured data on the medium (S102). A series of processing from step S101 to step S102 as described above is mainly realized by pre-processing unit 40 among various kinds of function units to be realized by computer 20.

In addition, when no data related to the desired testing content are found in data list 1e, the person in charge of testing pushes setup administration button 1c on measured data list screen 1 to open the administration screen, and can input the data of the desired testing content to add such data to data list 1e.

Figure 4C:
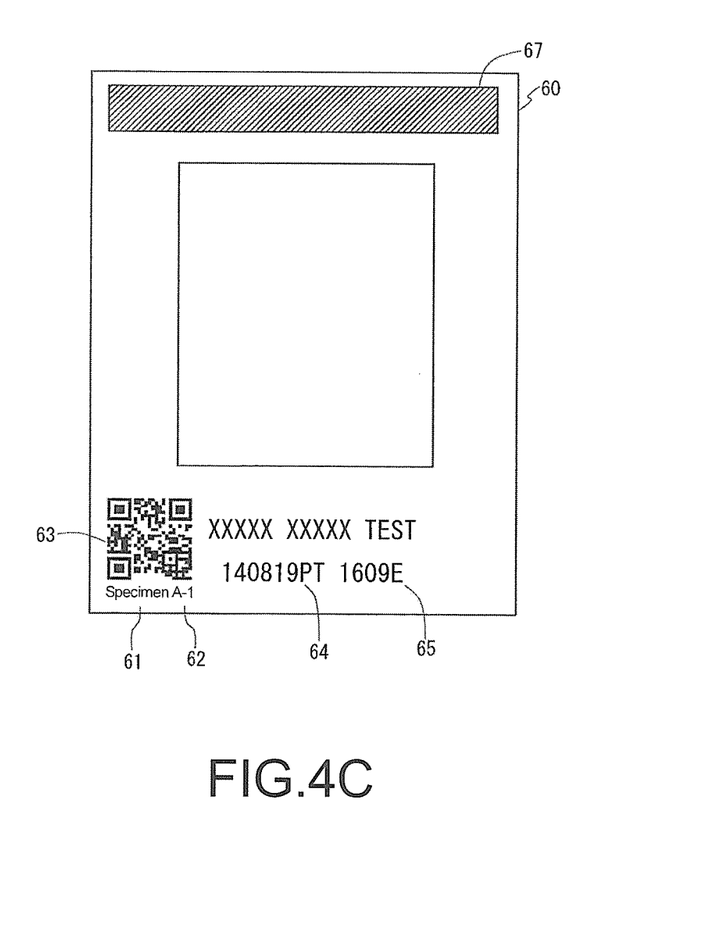
FIG. 4C is a diagram showing one example of a medium on which measured data are printed.

FIG. 4C is a diagram showing one example of the medium on which the measured data are printed. For example, as shown in FIG. 4C, on medium 60 on which printing is applied by combination machine 30, specimen name 61, dilution factor 62 and two-dimensional barcode 63 are printed. Two-dimensional barcode 63 is produced by coding the testing content shown by the measured data. The person in charge of testing uses medium 60 on which specimen name 61, dilution factor 62 and two-dimensional barcode 63 are printed, and performs dilution, inoculation and culture.

In addition, on medium 60, in addition to the information printed by combination machine 30, lot number 64, expiration date 65 of medium 60, and labelling 67 representing the type of the medium are originally printed.

Figure 4D:
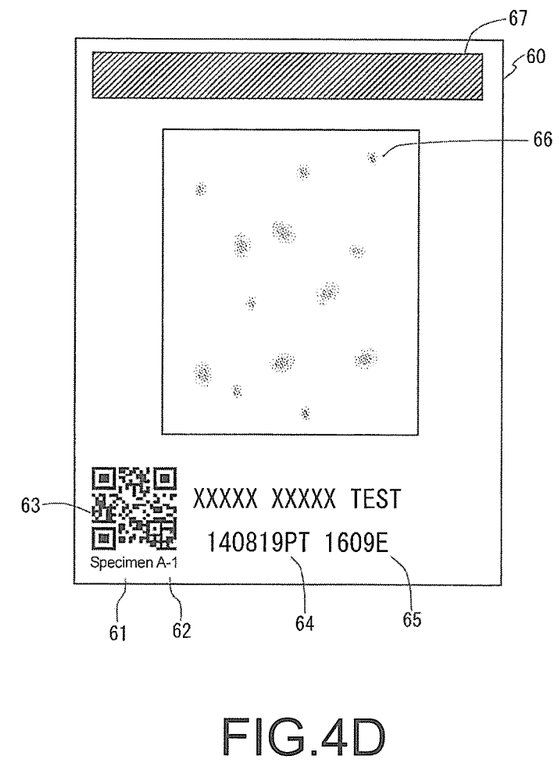
FIG. 4D is a diagram showing one example of a medium on which microorganisms are cultured.

FIG. 4D is a diagram showing one example of the medium on which the microorganisms are cultured. For example, as shown in FIG. 4D, on medium 60 on which the microorganisms are cultured, a great number of colonies 66 of the microorganisms are colored. The culture of microorganisms using medium 60 is completed, and then the person in charge of testing sets on combination machine 30 medium 60 on which a great number of colonies 66 of the microorganisms are colored. Then, if the person in charge of testing clicks measured data registration button 1*b* on the screen shown in FIG. 4A (S103), computer 20 performs processing described below.

More specifically, if measured data registration button 1*b* is clicked, computer 20 actuates combination machine 30 to read an image of medium 60. Then, computer 20 reads two-dimensional barcode 63 and expiration date 65 visible on the read image of medium 60. From data list 1*e*, computer 20 searches out data in agreement with the measured data obtained by decoding read two-dimensional barcode 63. Moreover, based on read expiration date 65, computer 20 judges whether or not medium 60 used in the testing has expired through the expiration date. Then, computer 20 displays a confirmation screen of measured data to be registered (S104).

Figure 4E:
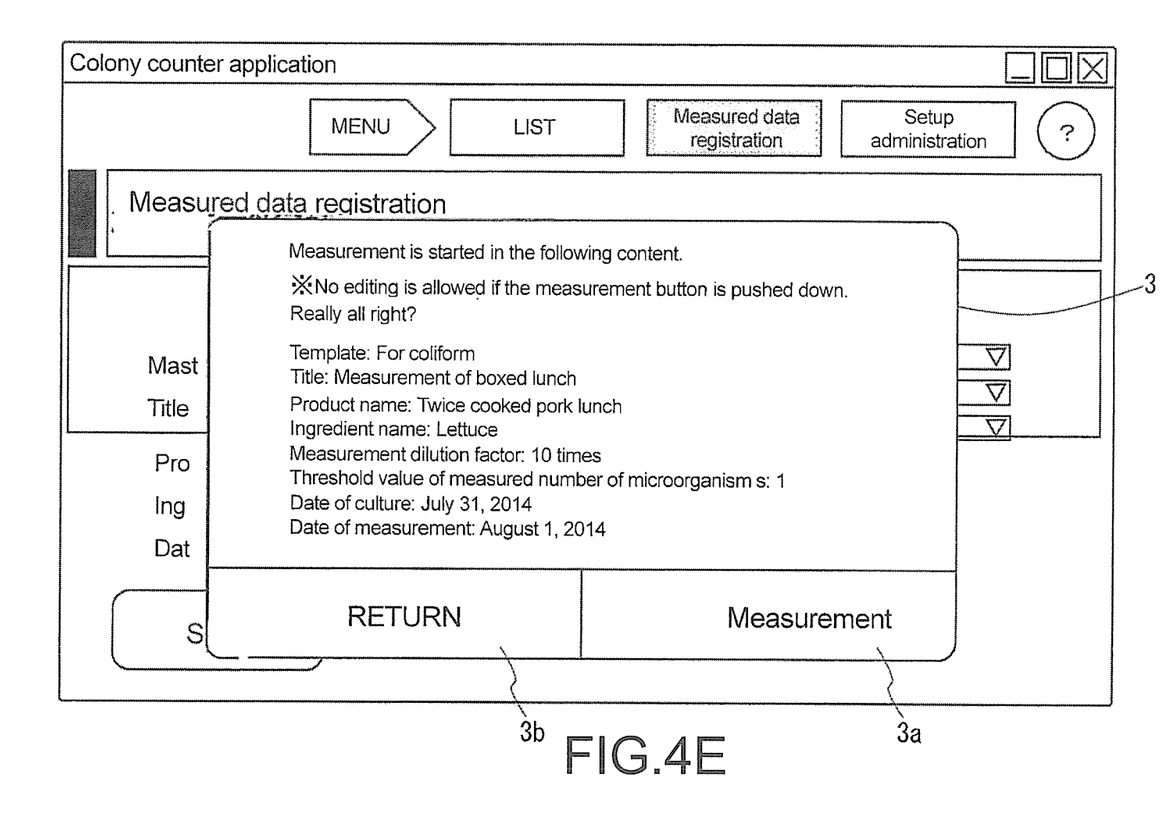
FIG. 4E is a diagram showing one example of a confirmation screen of measured data to be registered.

FIG. 4E is a diagram showing one example of the confirmation screen of the measured data to be registered. On confirmation screen 3 of the measured data to be registered, the product name and the ingredient name of the testing object, the dilution factor, the template name showing the kind of the medium to be used, the title, a date of culture and a date of measurement are displayed. The date of measurement refers to a date of a day on which registration work of the measured data is performed, and the date obtained from a clock built in computer 20. Moreover, on confirmation screen 3 of the measured data to be registered, measurement button 3*a* and return button 3*b* are displayed. If return button 3*b* is clicked, computer 20 deletes confirmation screen 3, and displays measured data list screen 1 being an original screen on the display device.

Figure 4F:
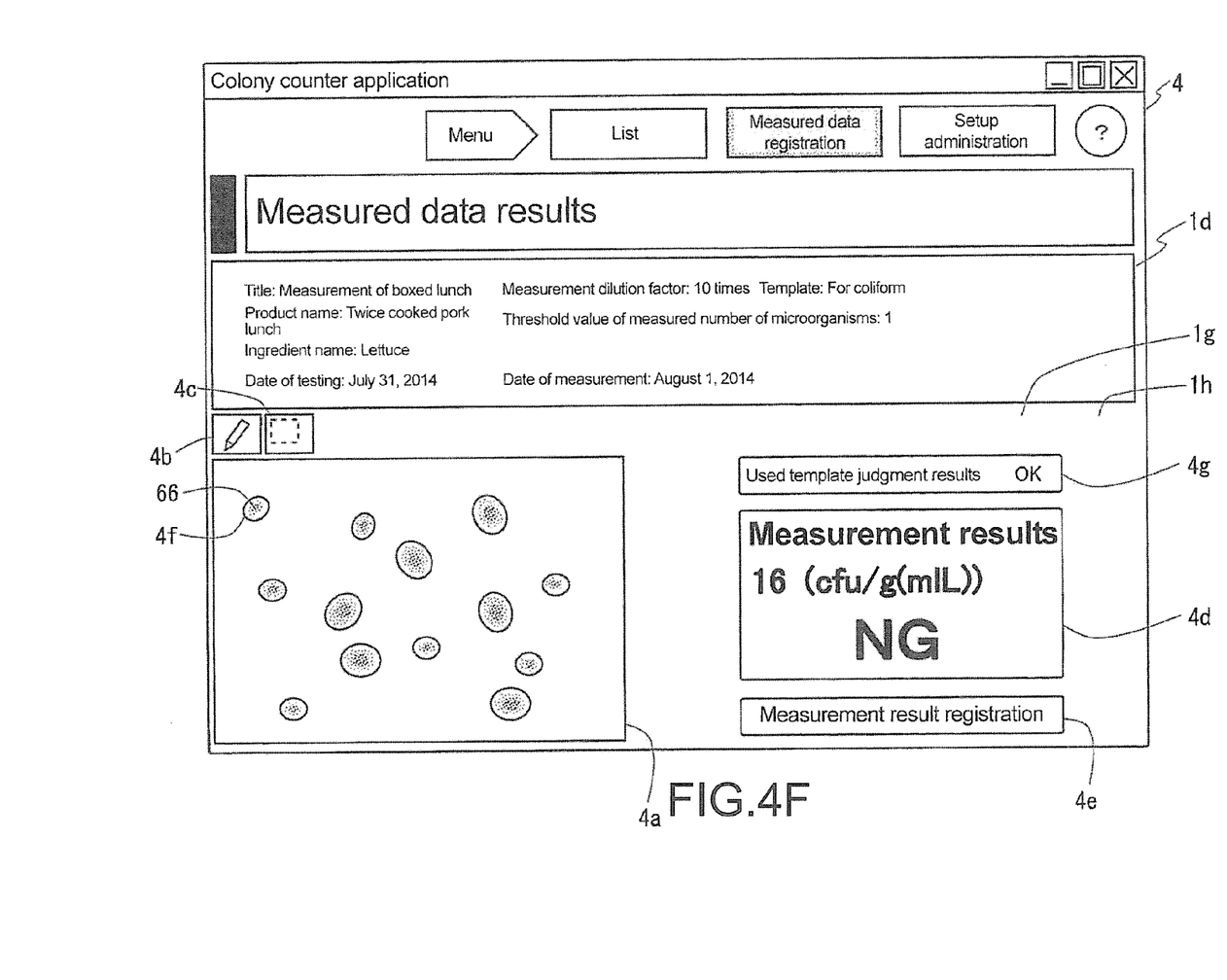
FIG. 4F is a diagram showing one example of a registration screen of measurement results.

FIG. 4F is a diagram showing one example of the registration screen of measurement results. If measurement button 3*a* is clicked on confirmation screen 3 as shown in FIG. 4E, computer 20 displays, on the display device, registration screen 4 arranging the product name and the ingredient name of the testing object, the dilution factor, the template name showing the kind of the medium to be used, the title, the date of culture and the date of measurement, and also image 4*a* of medium 60 read by combination machine 30, edit button 4*b*, measurement range change button 4*c*, measurement result field 4*d*, measurement result registration button 4*e* and used template judgment result field 4*g*. In image 4*a* of medium 60, ring-shaped mark 4*f* surrounding each of colonies 66 of microorganisms is provided. Mark 4*f* is provided for a colony identified as one of colonies 66 by computer 20 that analyzes image 4*a* after measurement button 3*a* is clicked. The measurement results in measurement result field 4*d* show the number of marks 4*f* identified as colonies 66 by computer 20 that analyzes image 4*a* after measurement button 3*a* is clicked, and judgment results obtained by comparing the number with the threshold value under conditions of judging the number of colonies specified by the testing content to be obtained by decoding two-dimensional barcode 63. Judgment results in used template judgment result field 4*g* show the judgment results obtained by collating, by computer 20 that analyzes image 4*a* after measurement button 3*a* is clicked, the testing content obtained by decoding two-dimensional barcode 63 with the type of medium 60 shown by labelling 67. In addition, with regard to the judgment results as to whether or not the expiration date of medium 60 acquired by reading expiration date 65 visible on image 4*a* has already passed, computer 20 may reflect such judgment results on the judgment results in used template judgment result field 4*g* or may display such judgment results on the judgment result field of the expiration date.

Figure 4G:
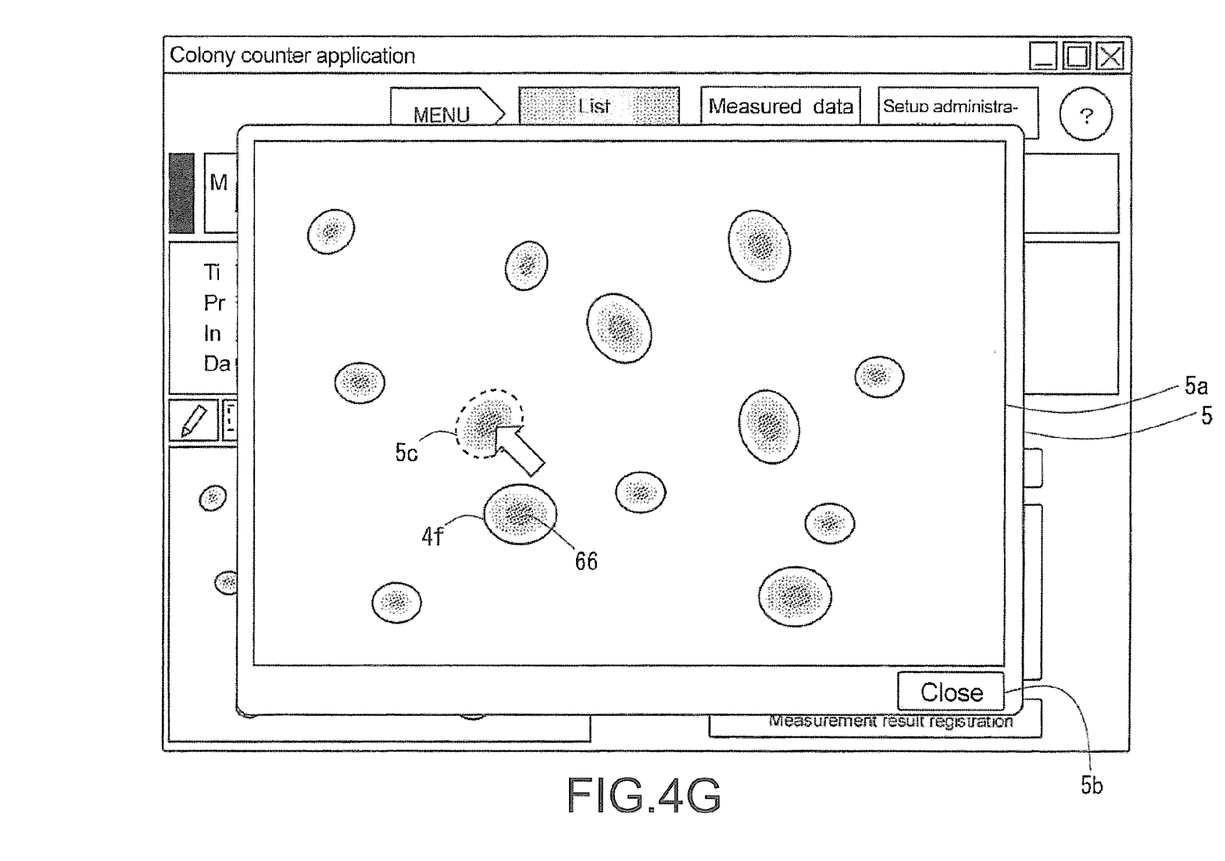
FIG. 4G is a diagram showing one example of a screen to be displayed upon pushing an edit button.

FIG. 4G is a diagram showing one example of a screen to be displayed upon pushing edit button 4*b*. If edit button 4*b* is clicked, computer 20 displays, on the display device, edit screen 5 arranging enlarged image 5*a* of medium 60 and close button 5*b*. Edit screen 5 is a screen for editing operation for cancelling mark 4*f* provided for a target identified as colonies 66 in image analysis, or providing a target unidentified as colonies 66 with mark 4*f*. Here, if any mark 4*f* displayed on image 4*a* is clicked, computer 20 changes clicked mark 4*f* into any other mark 5*c* different in color or linetype, or deletes mark 4*f*. Moreover, if close button 5*b* is clicked, computer 20 closes edit screen 5, and simultaneously counts colonies 66 provided with marks 4*f* in closed edit screen 5 to reflect the resulting value as the number of colonies in measurement result field 4*d* on registration screen 4 shown in FIG. 4F.

Figure 4H:
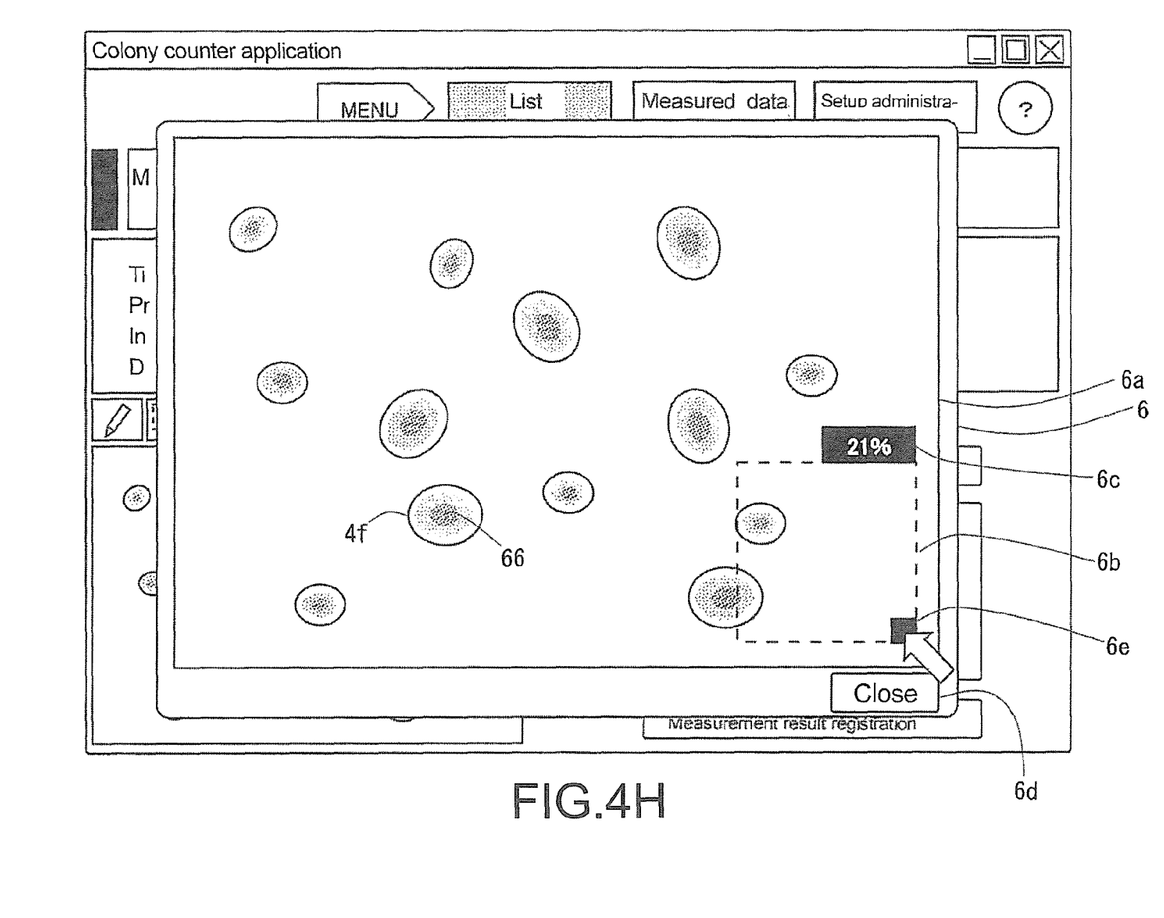
FIG. 4H is a diagram showing one example of a screen to be displayed upon pushing a measurement range change button.

FIG. 4H is a diagram showing one example of a screen to be displayed upon pushing measurement range change button 4*c*. If measurement range change button 4*c* is clicked, computer 20 displays, on the display device, measurement range change screen 6 arranging enlarged image 6*a* of medium 60, square range selection frame 6*b*, status bar 6*c* showing a ratio of a selected range of total in terms of percentage, and close button 6*d*. Measurement range change screen 6 is a screen for measurement range change operation for changing a measurement range of an image identified as colonies 66 in image analysis. Here, if small handle 6*e* in a lower right corner in range selection frame 6*b* is dragged, computer 20 enlarges or reduces range selection frame 6*b* to increase or decrease a value of status bar 6*c*. Moreover, if a frame border of range selection frame 6*b* is dragged, computer 20 moves range selection frame 6*b*. Moreover, if range selection frame 6*b* is dropped during enlarging or reducing or moving the frame 6*b*, computer 20 fixes a size and a position of range selection frame 6*b*. Moreover, if close button 6*d* is clicked, computer 20 closes measurement range change screen 6, and simultaneously counts colonies 66 provided with marks 4*f* in range selection frame 6*b* on closed measurement range change screen 6 to reflect the resulting value in measurement result field 4*d* on registration screen 4 shown in FIG. 4F.

If measurement result registration button 4*e* on registration screen 4 shown in FIG. 4F is clicked, computer 20 adds new measured data to a first row of data list 1*e* on measured data list screen 1 shown in FIG. 4A (S105). If measured data in an arbitrary row in data list 1*e* on measured data list screen 1 are clicked, the screen showing the results of measured data as shown in FIG. 4F is called and displayed on the display device. Accordingly, after the measured data are registered, the person in charge of testing can reconfirm image 4*a* of medium 60 and the measurement results at any time. In addition, a series of processing from step S103 to step S105 as described above is mainly realized by post-processing unit 50 among various kinds of function units to be realized by computer 20.

If microorganism testing apparatus 10 related to the embodiment is applied, the testing conditions are printed on the sheet-form medium to be used for testing of the specimen in the preparatory stage being pre-processing of the microorganism testing. Accordingly, if the person in charge of testing reads the testing conditions printed on the medium, the person can easily understand whether the medium is to be used for testing of any specimen. For example, such an error as the wrong use of different object upon handling the specimen and the medium can be suppressed. Further, microorganism testing apparatus 10 related to the embodiment analyzes the read image of the medium, in a data processing stage being post-processing of the microorganism testing, and collates the testing conditions printed on the medium with labelling 67 on the medium to output the results. Therefore, even if the wrong use of the medium occurs, microorganism testing apparatus 10 can detect the wrong use and inform the person in charge thereof of the fact. Moreover, if microorganism testing apparatus 10 related to the embodiment is applied, work in the preparatory stage of the microorganism testing is saved, and also information to be printed on the medium by realization of work saving is effectively used for verification of testing in the data processing stage being the post-processing of the microorganism testing. Thus, the pre-processing and the post-processing are organically associated with each other to achieve overall rationalization of the work related to testing of the microorganisms.

In addition, microorganism testing apparatus 10 related to the embodiment can also be modified as described below, for example. More specifically, microorganism testing apparatus 10 related to the embodiment may automatically judge whether or not the type of medium 60 set in combination machine 30 is compatible with the testing content to be printed, in the pre-processing in which printing is applied onto medium 60, and in case of negative judgment, suspend printing to display the judgment results on the screen, for example. The type of medium 60 set in combination machine 30 may be identified by reading labelling 67 preliminarily provided for medium 60 by the scanner function of combination machine 30 or any other scanner, or by alternating a shape or a size of medium 60 for every type, and using information on the shape or the size of medium 60 acquired from an image read by a sheet size discrimination function or the scanner in combination machine 30, for example. If microorganism testing apparatus 10 related to the embodiment is thus modified, culture of microorganisms using off-type medium 60 can be prevented.

Moreover, for example, when a plurality of sheet trays in which media before printing are set are equipped in combination machine 30 or the printer, microorganism testing apparatus 10 related to the embodiment may automatically select a sheet tray in which medium 60 to be compatible with the testing content to be printed is set to print the testing content on medium 60 set in the selected sheet tray. If microorganism testing apparatus 10 related to the embodiment is thus modified, work for exchanging media 60 is unnecessary in the preparatory work of the microorganism testing, and when a plurality of kinds of media 60 are handled in one-time preparatory work, the preparatory work is easy.

<Computer Readable Record Medium>

A program for realizing any function described above in a computer or any other machine or apparatus (hereinafter, referred to as a computer or the like) can be recorded on a computer or the like readable record medium. Then, the function can be provided by allowing the computer or the like to read and execute the program on the record medium.

Here, the computer or the like readable record medium means a record medium in which information such as data and the program can be accumulated by electrical, magnetic, optical, mechanical or chemical action, and read from the computer or the like. Specific examples of media detachable from the computer or the like among such record media include a flexible disc, a magnetic optical disc, CD-ROM, CD-R/W, DVD, a Blu-ray disc (Blu-ray is a registered trademark), DAT, an 8 mm tape and a memory card such as a flash memory. Moreover, specific examples of the record medium fixed to the computer or the like include a hard disk and ROM (read only memory).

In addition, the present disclosure includes appendant items described below.

Item 1. A microorganism testing apparatus, comprising:
a pre-processing unit in which, if a content of microorganism testing on a specific specimen is selected or input, testing conditions of the specific specimen read from a storage device in which testing information specifying the testing conditions of the specimen is stored are printed on a sheet-form medium to be used for testing of the specific specimen; and
a post-processing unit in which, if an image of the medium is read, the testing conditions printed on the medium and a type of the medium preliminarily labelled on the medium are acquired from the image to output judgment results as to whether or not the testing conditions acquired from the image, and the type of the medium are compatible.

Item 2. The microorganism testing apparatus according to item 1, wherein the pre-processing unit prints a symbol or a name representing the specific specimen, a dilution factor and a code produced by coding any other testing condition.

Item 3. The microorganism testing apparatus according to item 1 or 2, wherein an expiration date of the medium is preliminarily displayed on the medium, and
the post-processing unit further acquires, if the image of the medium is read, the expiration date displayed on the medium from the image to further output judgment results as to whether or not the expiration date acquired from the image has passed.

Item 4. The microorganism testing apparatus according to any one of items 1 to 3, wherein the post-processing unit specifies, if the image is read, the number of colonies grown on the medium, from the image.

Item 5. The microorganism testing apparatus according to item 4, wherein a threshold value of quality determination of the number of colonies is further predetermined in the testing conditions, and
the post-processing unit outputs tested results of the specific specimen based on the specified number of colonies and the threshold value in the testing conditions.

Item 6. The microorganism testing apparatus according to any one of items 1 to 5, wherein the pre-processing unit reads, if the content of microorganism testing on the specific specimen is selected or input, an image of the medium to be printed, or discriminates a shape or a size of the medium to be printed to further judge whether or not the testing conditions of the specific specimen read from the storage device, and a type of the medium to be printed are compatible.

Item 7. The microorganism testing apparatus according to any one of items 1 to 5, wherein the pre-processing unit selects, if the content of microorganism testing on the specific specimen is selected or input, a medium compatible with the testing conditions of the specific specimen read from the storage device from a plurality of kinds of media preliminarily arranged for a device for applying printing onto the medium to print the testing conditions on a selected medium.

Item 8. A microorganism testing method, comprising:
performing a pre-processing step, in which, if a content of microorganism testing on a specific specimen is selected or input, testing conditions of the specific specimen read from a storage device in which testing information specifying the testing conditions of the specimen is stored are printed on a sheet-form medium to be used for testing of the specific specimen; and
performing a post-processing step, in which, if an image of the medium is read, the testing conditions printed on the medium and a type of the medium preliminarily labelled on the medium are acquired from the image to output judgment results as to whether or not the testing conditions acquired from the image, and the type of the medium are compatible.

Item 9. The microorganism testing method according to item 8, wherein, upon the pre-processing step, a symbol or a name representing the specific specimen, a dilution factor and a code produced by coding any other testing condition are printed.

Item 10. The microorganism testing method according to item 8 or 9, wherein an expiration date of the medium is preliminarily displayed, on the medium, and
upon the post-processing step, if the image of the medium is read, the expiration date displayed on the medium is further acquired from the image to further output judgment results as to whether or not the expiration date acquired from the image has passed.

Item 11. The microorganism testing method according to any one of items 8 to 10, wherein, upon the post-processing step, if the image is read, the number of colonies grown on the medium is specified from the image.

Item 12. The microorganism testing method according to item 11, wherein a threshold value of quality determination of the number of colonies is further predetermined in the testing conditions, and
upon the post-processing step, tested results of the specific specimen are output based on the specified number of colonies and the threshold value in the testing conditions.

Item 13. The microorganism testing method according to any one of items 8 to 12, wherein, upon the pre-processing step, if the content of microorganism testing on the specific specimen is selected or input, an image of the medium to be printed is read, or a shape or a size of the medium to be printed is discriminated to further judge whether or not the testing conditions of the specific specimen read from the storage device, and a type of the medium to be printed are compatible.

Item 14. The microorganism testing method according to any one of items 8 to 12, wherein, upon the pre-processing step, if the content of microorganism testing on the specific specimen is selected or input, a medium compatible with the testing conditions of the specific specimen read from the storage device is selected from a plurality of kinds of media preliminarily arranged for a device for applying printing onto the medium to print the testing conditions on a selected medium.

Item 15. A non-transitory computer-readable recording medium having stored therein a microorganism testing program, allowing a computer to execute:
a pre-processing step, in which, if a content of microorganism testing on a specific specimen is selected or input, testing conditions of the specific specimen read from a storage device in which testing information specifying the testing conditions of the specimen is stored are printed on a sheet-form medium to be used for testing of the specific specimen; and
a post-processing step, in which, if an image of the medium is read, the testing conditions printed on the medium and a type of the medium preliminarily labelled on the medium are acquired from the image to output judgment results as to whether or not the testing conditions acquired from the image, and the type of the medium are compatible.

Item 16. The non-transitory computer-readable recording medium having stored therein the microorganism testing program according to item 15, wherein, upon the pre-processing step, a symbol or a name representing the specific specimen, a dilution factor and a code produced by coding any other testing condition are printed.

Item 17. The non-transitory computer-readable recording medium having stored therein the microorganism testing program according to item 15 or 16, wherein an expiration date of the medium is preliminarily displayed, on the medium, and
upon the post-processing step, if an image of the medium is read, the expiration date displayed on the medium is further acquired from the image to further output judgment results as to whether or not the expiration date acquired from the image has passed.

Item 18. The non-transitory computer-readable recording medium having stored therein the microorganism testing program according to any one of items 15 to 17, wherein, upon the post-processing step, if the image is read, the number of colonies grown on the medium is specified from the image.

Item 19. The non-transitory computer-readable recording medium having stored therein the microorganism testing program according to item 18, wherein a threshold value of quality determination of the number of colonies is further predetermined in the testing conditions, and
upon the post-processing step, tested results of the specific specimen are output based on the specified number of colonies and the threshold value in the testing conditions.

Item 20. The non-transitory computer-readable recording medium having stored therein the microorganism testing program according to any one of items 15 to 19, wherein, upon the pre-processing step, if the content of microorganism testing on the specific specimen is selected or input, an image of the medium to be printed is read, or a shape or a size of the medium to be printed is discriminated to further judge whether or not the testing conditions of the specific specimen read from the storage device, and a type of the medium to be printed are compatible.

Item 21. The non-transitory computer-readable recording medium having stored therein the microorganism testing program according to any one of items 15 to 19, wherein, upon the pre-processing step, if the content of microorganism testing on the specific specimen is selected or input, a medium compatible with the testing conditions of the specific specimen read from the storage device is selected from a plurality of kinds of media preliminarily arranged for a device for applying printing onto the medium to print the testing conditions on a selected medium.

What is claimed is:

1. A microorganism testing apparatus, comprising:
a pre-processing unit in which, if a content of microorganism testing on a specific specimen is selected or input, testing conditions of the specific specimen read from a storage device in which testing information specifying the testing conditions of the specimen is stored are printed on a sheet-form medium to be used for testing of the specific specimen; and
a post-processing unit in which, if an image of the medium is read, the testing conditions printed on the medium and a type of the medium preliminarily labelled on the medium are acquired from the image to output judgment results as to whether or not the testing conditions acquired from the image, and the type of the medium are compatible.

2. The microorganism testing apparatus according to claim 1, wherein the pre-processing unit prints a symbol or a name representing the specific specimen, a dilution factor and a code produced by coding any other testing condition.

3. The microorganism testing apparatus according to claim 1, wherein an expiration date of the medium is preliminarily displayed, on the medium, and
the post-processing unit further acquires, if the image of the medium is read, the expiration date displayed on the medium from the image to further output judgment results as to whether or not the expiration date acquired from the image has passed.

4. The microorganism testing apparatus according to claim 1, wherein the post-processing unit specifies, if the image is read, the number of colonies grown on the medium, from the image.

5. The microorganism testing apparatus according to claim 4, wherein a threshold value of quality determination of the number of colonies is further predetermined in the testing conditions, and
the post-processing unit outputs tested results of the specific specimen based on the specified number of colonies and the threshold value in the testing conditions.

6. The microorganism testing apparatus according to claim 1, wherein the pre-processing unit reads, if the content of microorganism testing on the specific specimen is selected or input, an image of the medium to be printed, or discriminates a shape or a size of the medium to be printed to further judge whether or not the testing conditions of the specific specimen read from the storage device, and a type of the medium to be printed are compatible.

7. The microorganism testing apparatus according to claim 1, wherein the pre-processing unit selects, if the content of microorganism testing on the specific specimen is selected or input, a medium compatible with the testing conditions of the specific specimen read from the storage device from a plurality of kinds of media preliminarily arranged for a device for applying printing onto the medium to print the testing conditions on a selected medium.

8. A microorganism testing method, comprising:
performing a pre-processing step, in which, if a content of microorganism testing on a specific specimen is selected or input, testing conditions of the specific specimen read from a storage device in which testing information specifying the testing conditions of the specimen is stored are printed on a sheet-form medium to be used for testing of the specific specimen; and
performing a post-processing step, in which, if an image of the medium is read, the testing conditions printed on the medium and a type of the medium preliminarily labelled on the medium are acquired from the image to output judgment results as to whether or not the testing conditions acquired from the image, and the type of the medium are compatible.

9. The microorganism testing method according to claim 8, wherein, upon the pre-processing step, a symbol or a name representing the specific specimen, a dilution factor and a code produced by coding any other testing condition are printed.

10. The microorganism testing method according to claim 8, wherein an expiration date of the medium is preliminarily displayed, on the medium, and
upon the post-processing step, if the image of the medium is read, the expiration date displayed on the medium is further acquired from the image to further output judgment results as to whether or not the expiration date acquired from the image has passed.

11. The microorganism testing method according to claim 8, wherein, upon the post-processing step, if the image is read, the number of colonies grown on the medium is specified from the image.

12. The microorganism testing method according to claim 11, wherein a threshold value of quality determination of the number of colonies is further predetermined in the testing conditions, and
upon the post-processing step, tested results of the specific specimen are output based on the specified number of colonies and the threshold value in the testing conditions.

13. The microorganism testing method according to claim 8, wherein, upon the pre-processing step, if the content of microorganism testing on the specific specimen is selected or input, an image of the medium to be printed is read, or a shape or a size of the medium to be printed is discriminated to further judge whether or not the testing conditions of the specific specimen read from the storage device, and a type of the medium to be printed are compatible.

14. The microorganism testing method according to claim 8, wherein, upon the pre-processing step, if the content of microorganism testing on the specific specimen is selected or input, a medium compatible with the testing conditions of the specific specimen read from the storage device is selected from a plurality of kinds of media preliminarily arranged for a device for applying printing onto the medium to print the testing conditions on a selected medium.

15. A non-transitory computer-readable recording medium having stored therein a microorganism testing program, allowing a computer to execute:
a pre-processing step, in which, if a content of microorganism testing on a specific specimen is selected or input, testing conditions of the specific specimen read from a storage device in which testing information specifying the testing conditions of the specimen is stored are printed on a sheet-form medium to be used for testing of the specific specimen; and
a post-processing step, in which, if an image of the medium is read, the testing conditions printed on the medium and a type of the medium preliminarily labelled on the medium are acquired from the image to output judgment results as to whether or not the testing conditions acquired from the image, and the type of the medium are compatible.

16. The non-transitory computer-readable recording medium having stored therein the microorganism testing program according to claim 15, wherein, upon the pre-processing step, a symbol or a name representing the specific specimen, a dilution factor and a code produced by coding any other testing condition are printed.

17. The non-transitory computer-readable recording medium having stored therein the microorganism testing program according to claim 15, wherein an expiration date of the medium is preliminarily displayed on the medium, and upon the post-processing step, if an image of the medium is read, the expiration date displayed on the medium is further acquired from the image to further output judgment results as to whether or not the expiration date acquired from the image has passed.

18. The non-transitory computer-readable recording medium having stored therein the microorganism testing program according to claim 15, wherein, upon the post-processing step, if the image is read, the number of colonies grown on the medium is specified from the image.

19. The non-transitory computer-readable recording medium having stored therein the microorganism testing program according to claim 18, wherein a threshold value of quality determination of the number of colonies is further predetermined in the testing conditions, and upon the post-processing step, tested results of the specific specimen are output based on the specified number of colonies and the threshold value in the testing conditions.

20. The non-transitory computer-readable recording medium having stored therein the microorganism testing program according to claim 15, wherein, upon the pre-processing step, if the content of microorganism testing on the specific specimen is selected or input, an image of the medium to be printed is read, or a shape or a size of the medium to be printed is discriminated to further judge whether or not the testing conditions of the specific specimen read from the storage device, and a type of the medium to be printed are compatible.

21. The non-transitory computer-readable recording medium having stored therein the microorganism testing program according to claim 15, wherein, upon the pre-processing step, if the content of microorganism testing on the specific specimen is selected or input, a medium compatible with the testing conditions of the specific specimen read from the storage device is selected from a plurality of kinds of media preliminarily arranged for a device for applying printing onto the medium to print the testing conditions on a selected medium.

* * * * *